US012290297B2

(12) United States Patent
Leff et al.

(10) Patent No.: US 12,290,297 B2
(45) Date of Patent: May 6, 2025

(54) SYSTEMS AND METHODS FOR THREE DIMENSIONAL RECONSTRUCTION OF A BENT ROD USED IN SURGERY

(71) Applicant: GLOBUS MEDICAL, INC., Audubon, PA (US)

(72) Inventors: David Leff, Philadelphia, PA (US); Samuel Paster, Jamaica Plain, MA (US)

(73) Assignee: Globus Medical, Inc., Audubon, PA (US)

( * ) Notice: Subject to any disclaimer, the term of this patent is extended or adjusted under 35 U.S.C. 154(b) by 354 days.

(21) Appl. No.: 17/735,467

(22) Filed: May 3, 2022

(65) Prior Publication Data
US 2023/0355289 A1 Nov. 9, 2023

(51) Int. Cl.
*A61B 17/00* (2006.01)
*A61B 17/88* (2006.01)
*A61B 34/20* (2016.01)

(52) U.S. Cl.
CPC .. *A61B 17/8863* (2013.01); *A61B 2034/2055* (2016.02); *A61B 2034/2068* (2016.02)

(58) Field of Classification Search
None
See application file for complete search history.

(56) References Cited

U.S. PATENT DOCUMENTS

| 2017/0042597 A1* | 2/2017 | Rinner | A61B 17/8863 |
| 2018/0055546 A1* | 3/2018 | Beger | A61F 2/4455 |
| 2022/0047336 A1* | 2/2022 | Boehler | A61B 34/20 |

* cited by examiner

*Primary Examiner* — Paul B Yanchus, III

(57) ABSTRACT

A rod bender includes a first handle arm and a second handle arm coupled to a first pivot point. A body portion of the rod bender is coupled to the first handle arm at a second pivot point and the second handle arm is coupled to the body portion at a third pivot point. The body portion also includes first and second distal arms configured with first and second rolling elements and navigation arrays coupled to distal ends of the first and second distal arms. A barrel is provided on the body portion which is positioned on a center area of the body portion. The navigation arrays have optical markers that are tracked by camera. A three-dimensional reconstruction of a rod bent by the rod bender is created using tracked position of the optical markers during bending.

20 Claims, 12 Drawing Sheets

SYSTEMS AND METHODS FOR THREE DIMENSIONAL RECONSTRUCTION OF A BENT ROD USED IN SURGERY

FIELD OF THE DISCLOSURE

The disclosure relates to a system and method for bending elongated spinal rods and plates and creating a three dimensional reconstruction on the bent rod to enable software to measure the contour.

BACKGROUND OF THE DISCLOSURE

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. Devices such as rods and plates are utilized to stabilize adjacent vertebrae. However, these rods and plates need to be bent or modified to accommodate the anatomy.

Spinal rods are used to connect pedicle screws rigidly into a uniform construct and contoured to match patient anatomy. The rods may also be overcontoured to sit above a patient's spine to pull the spine into alignment using corrective instruments. Sometimes a user may use a malleable rod template to get a visual representation of the desired rod geometry to assist in bending a rod to match the designed rod template. Manual bending methods are currently used to shape these rods with user variability playing significantly into the resulting rod contour. Therefore, there is a need for a device which allows a surgeon to easily and accurately bend spinal rods and plates prior to insertion in to the body and creating a digital three dimensional (3D) reconstruction of the rod or rod template geometry that enables software to measure a contoured rod.

SUMMARY OF THE DISCLOSURE

To meet this and other needs, a rod bender system is provided. The rod bender system includes a first handle arm and a second handle arm coupled to a first pivot point, a body portion coupled to the first handle arm at a second pivot point and the second handle arm coupled to the body portion at a third pivot point. The body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion. A spinal rod having a third navigation array having one or more optical markers is positioned between the first and second rolling elements and the barrel. A shape of the rod as it is being bent is trackable by a camera system using the optical markers and a three dimensional reconstruction of the rod is created using tracked positions of the optical markers.

Also provided is a spinal rod bending system including an elongated spinal rod, a camera, and a rod bender for manipulating an elongated spinal rod including. The rod bender including a first handle arm and a second handle arm coupled to a first pivot point, and a body portion coupled to the first handle arm at a second pivot point and the second handle arm coupled to the body portion at a third pivot point. The body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion. A spinal rod having a third navigation array having one or more optical markers is positioned between the first and second rolling elements and the barrel. A shape of the rod as it is being bent is trackable by the camera using the optical markers and a three dimensional reconstruction of the rod is created using tracked positions of the optical markers.

Also provided is a method for manipulating a spinal rod including providing a rod bender. The rod bender includes a first handle arm and a second handle arm coupled to a first pivot point, a body portion coupled to the first handle arm at a second pivot point and the second handle arm coupled to the body portion at a third pivot point. The body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion. The method further includes positioning the spinal rod, having a third navigation array with one or more optical markers attached to a base of the spinal rod, between the rolling elements and the barrel of the rod bender, actuating the first and second handle arms thereby bending the spinal rod, tracking a shape of the spinal rod as it is being bent via a camera using the optical markers, and creating a three dimensional reconstruction of the spinal rod using tracked positions of the optical markers.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced.

DETAILED DESCRIPTION OF THE DISCLOSURE

While it is apparent that the invention disclosed herein is well calculated to fulfill the objects stated above, it will be appreciated that numerous modifications and embodiments may be devised by those skilled in the art.

Figure 1:
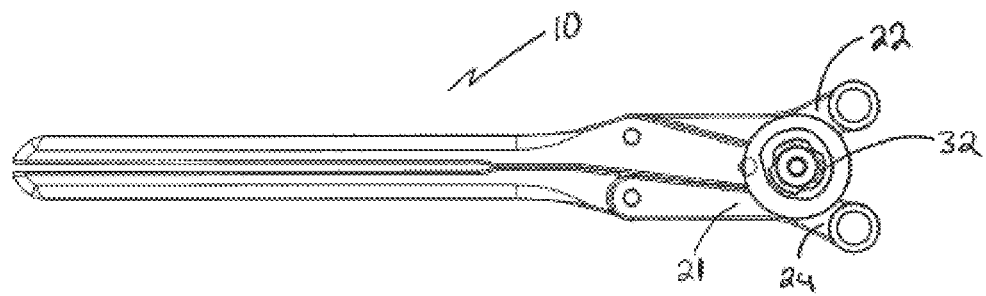
FIG. 1 is a compound rod bender according to the present invention in a closed position.
Figure 2:
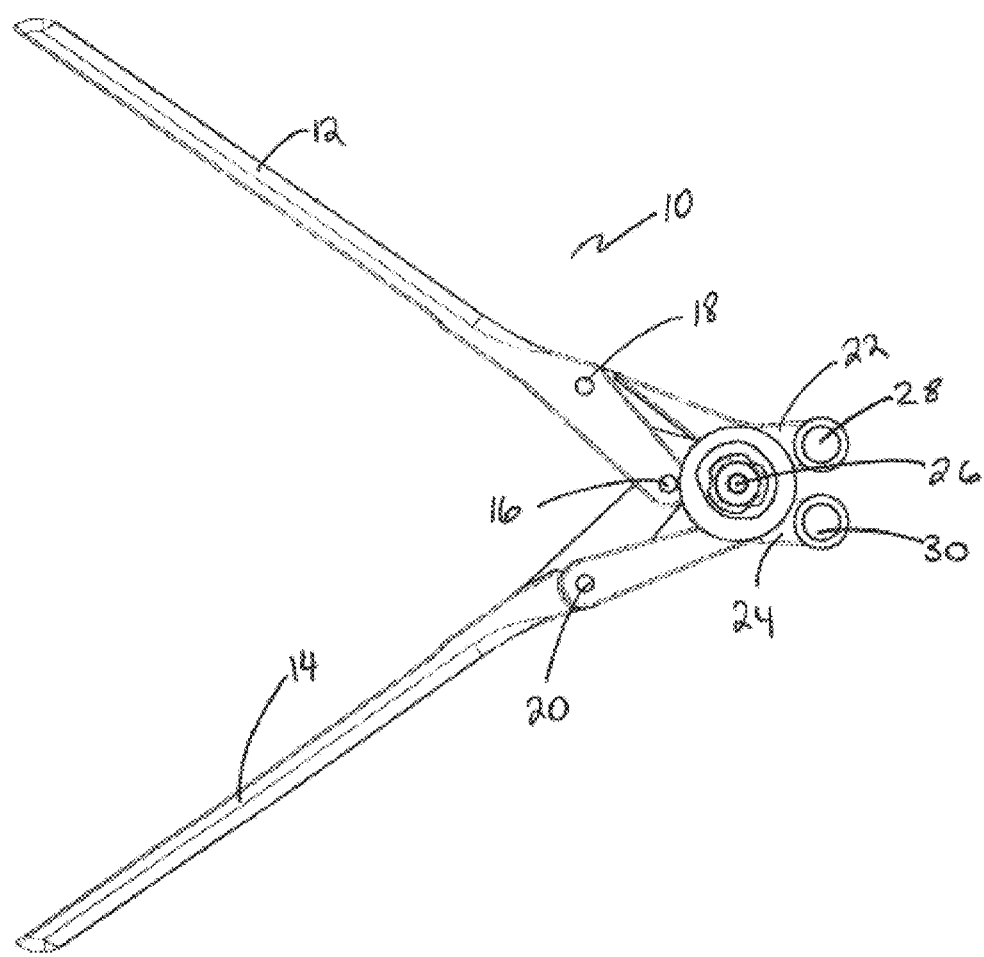
FIG. 2 is a compound rod bender according to the present invention in an open position.
Figure 3:
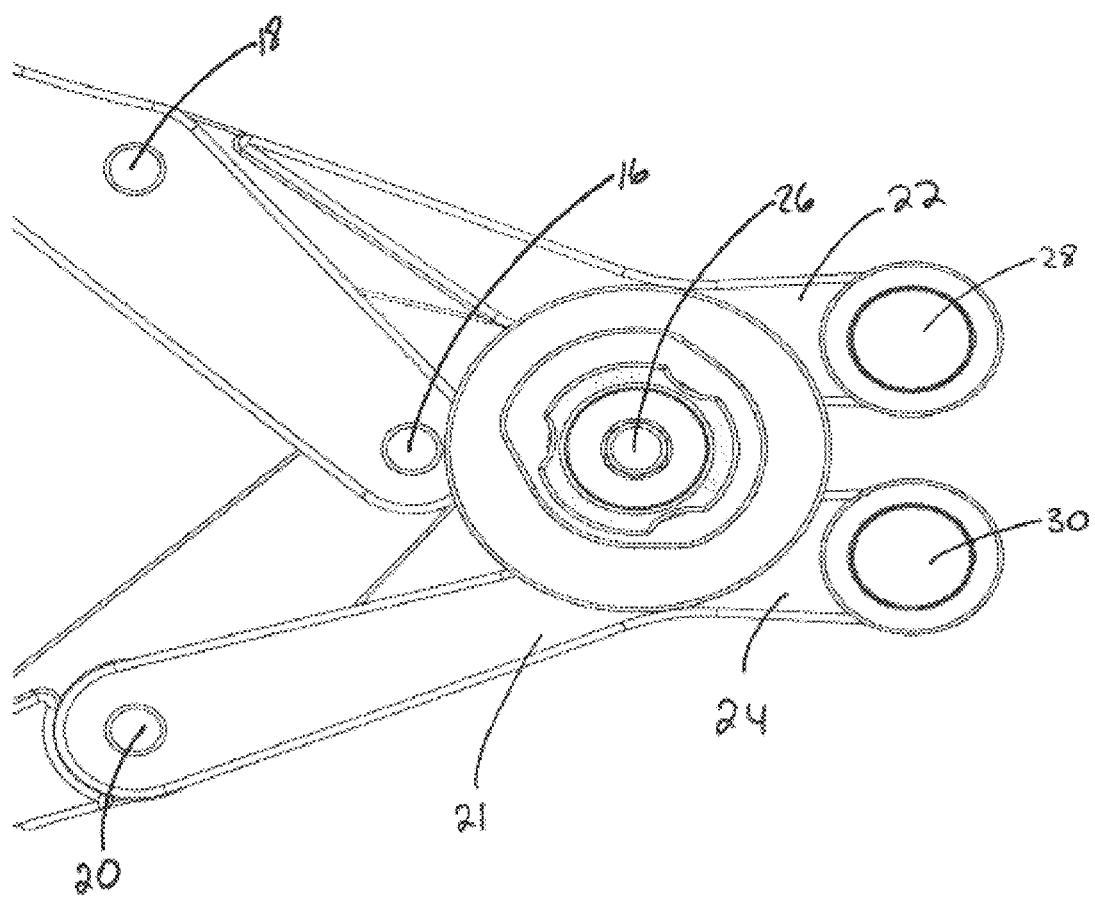
FIG. 3 is a top view of the body portion of the compound rod bender according to the present disclosure.
Figure 4:
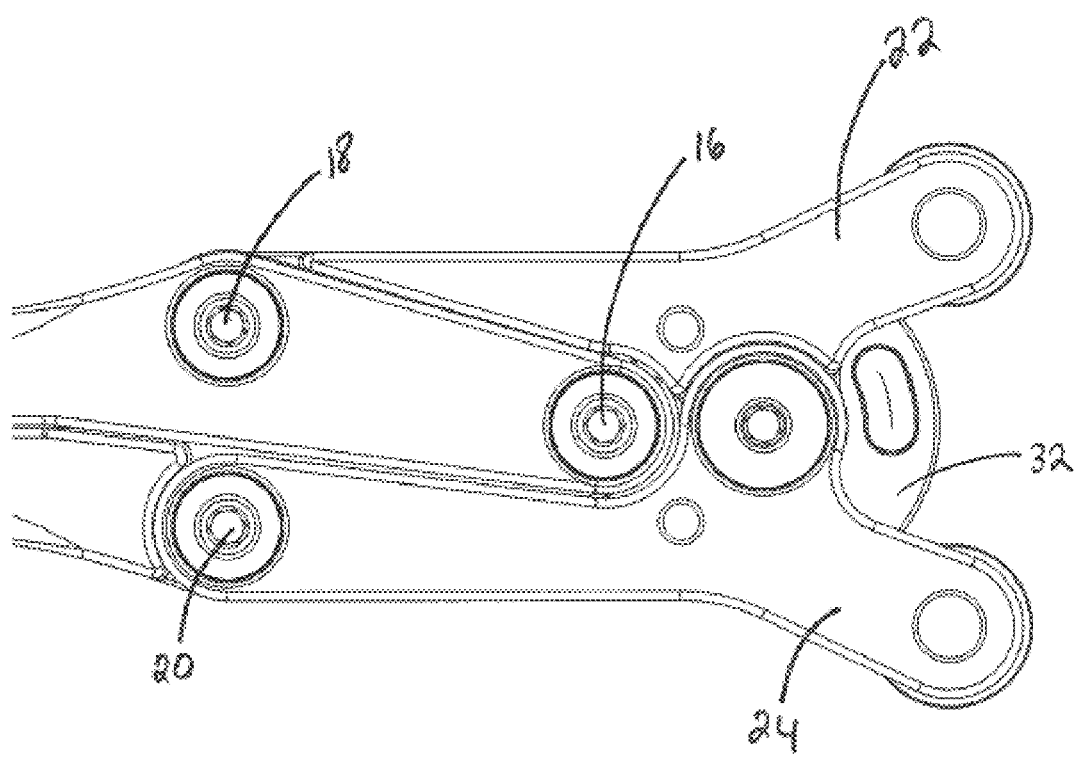
FIG. 4 is a bottom view of the body portion of the compound rod bender in a closed position according to the present disclosure.
Figure 5:
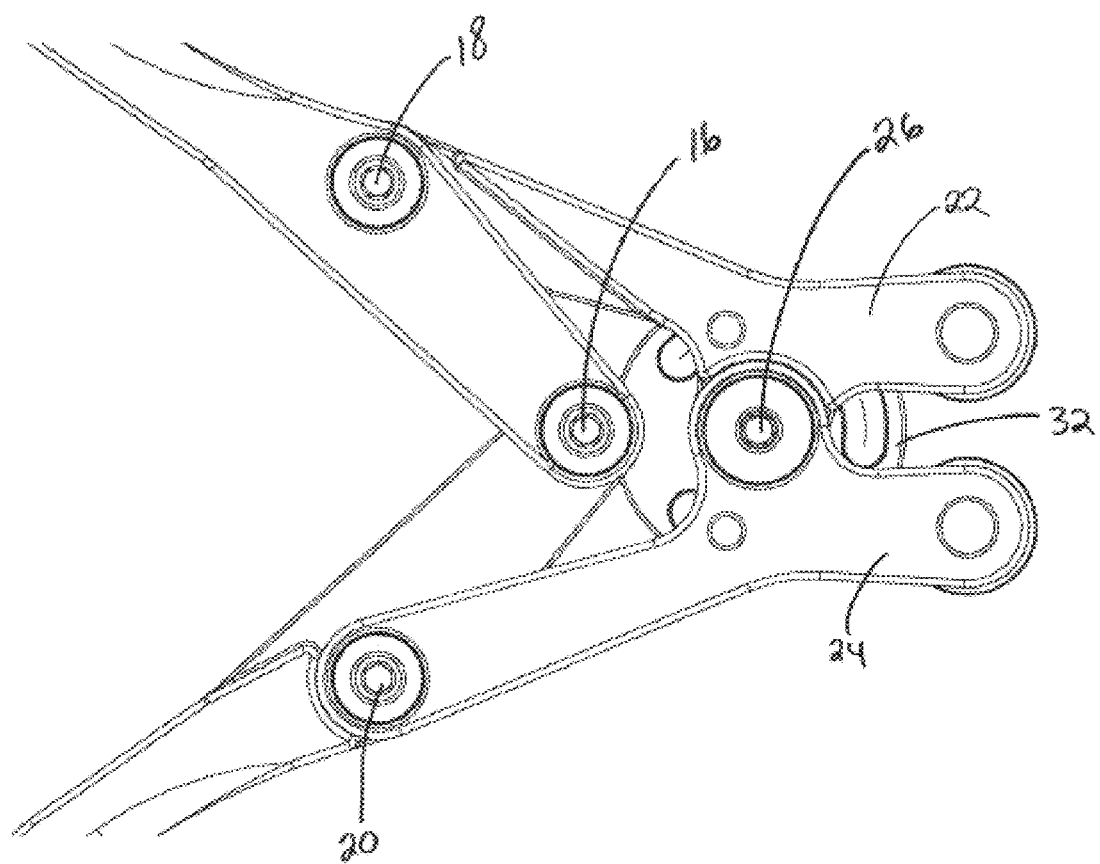
FIG. 5 is a bottom view of the compound rod bender in an open position according to the present disclosure.

FIGS. 1 and 2 illustrate a compound rod bender 10 in a closed position and in an open position. FIGS. 3-5 illustrate a top view and the bottom view of the rod bender in greater detail. Turning to FIGS. 1-5, the rod bender 10 comprises a first handle arm 12 and a second handle arm 14 that are coupled at a pivot point 16 and pivot points 18 and 20. The first handle arm 12 and the second handle arm 14 are connected to the body 21 of the compound rod bender 10 at pivot points 18 and 20, respectively. The rod bender 10 also comprises a first distal arm 22 and a second distal arm 24 which are configured about pivot point 26. The body 21 of the rod bender 10 is further provided with a first rolling element 28 and a second rolling element 30. The first rolling element 28 is positioned on the distal end of the first distal arm 22 and is configured to be rotatable. The second rolling element 30 is positioned on the distal end of the second distal arm 24 and is configured to be rotatable. The body 21 further provides a rotatable barrel 32 positioned below the first and second rolling elements 28 and 30. The rolling elements 28 and 30 are configured with rotating outer bearing portions which are substantially circular which are coupled to the first and second distal arms by a pin.

The barrel 32 is provided to support a rod when the rod is positioned between the rolling elements and the distal end of the barrel 32. The barrel 32 which is positioned on the pivot point 26 acts as a hinge between the two distal arms 22 and 24. The base portion of the barrel 32 includes a plurality of bending surfaces. Each bending surface can be selectively positioned into the desired operating position. The variety of bending surface contours enables the rod bender to accommodate different size rods, as well as provides for varying severities or contours of bend to the rod. The barrel 32 can be selectively rotated to cause the desired bending surface to be in appropriate position. During the operation of the rod bender 10, when the first and second handle arms 12 and 14 are actuated, a rod that is positioned in the rod bender is bent to accommodate the surgeon's preference. The radius of the bend in the rod can be manipulated by turning the barrel to various positions, as the circumference of the barrel is configured with different radii.

Operation of rod bender 10 begins with the desired bending surface on the barrel rotated and engaged into the operating position. The selected surface of the barrel faces toward the distal end of the instrument and operator positions a spinal rod between the rolling elements and the barrel after the handle arms of the instrument are moderately separated. This causes the distal arms to rotate in an arc upward and inward providing vertical clearance between the two distal arms and the barrel. After clearance is obtained, a suitable rod is then placed onto the selected bending surface of the barrel and the under the first and second rolling elements. A slight grip by the hands of the user will bring the distal arms and the rolling elements down and against the rod trapping it against the bending surface of the barrel. Additional force will bend the rod around the bending surface of the barrel. If a more or less severe bend is desired, the barrel can be rotated so that a different bending surface can be used.

The present disclosure includes the use of a compound hinge to increase the instruments mechanical advantage. The introduction of three additional pivot points and two lever arms will increase the instrument's output force dramatically, reducing the force required to contour a surgical rod when compared to a traditional rod bender. The relationship between the two sets of lever arms is directly related to the instrument's output force. It uses a compound joint to increase the bending force.

Turning now to FIGS. 6-11, illustrated are systems and methods that allow the ability to measure the three dimensional (3D) shape of a bent rod. This enables software to evaluate the 3D shape of the rod against a planned rod or idealized rod shape, assist the user in adjusting bends in the rod, or verify that an automatically bent rod matches the designed rod geometry. Advanced computational models may be able to determine how well a rod matches the contour of the spine and the amount of overcontour that will result in correction of the spine.

The described embodiment may use optical tracking and image processing techniques. Some embodiments require minimal user interaction to scan the rod while some embodiments may have a user manually trace the rod contour. The use of optical tracking and image processing may increase accuracy of the bent rod to conform to the planned rod shape.

Figure 6:
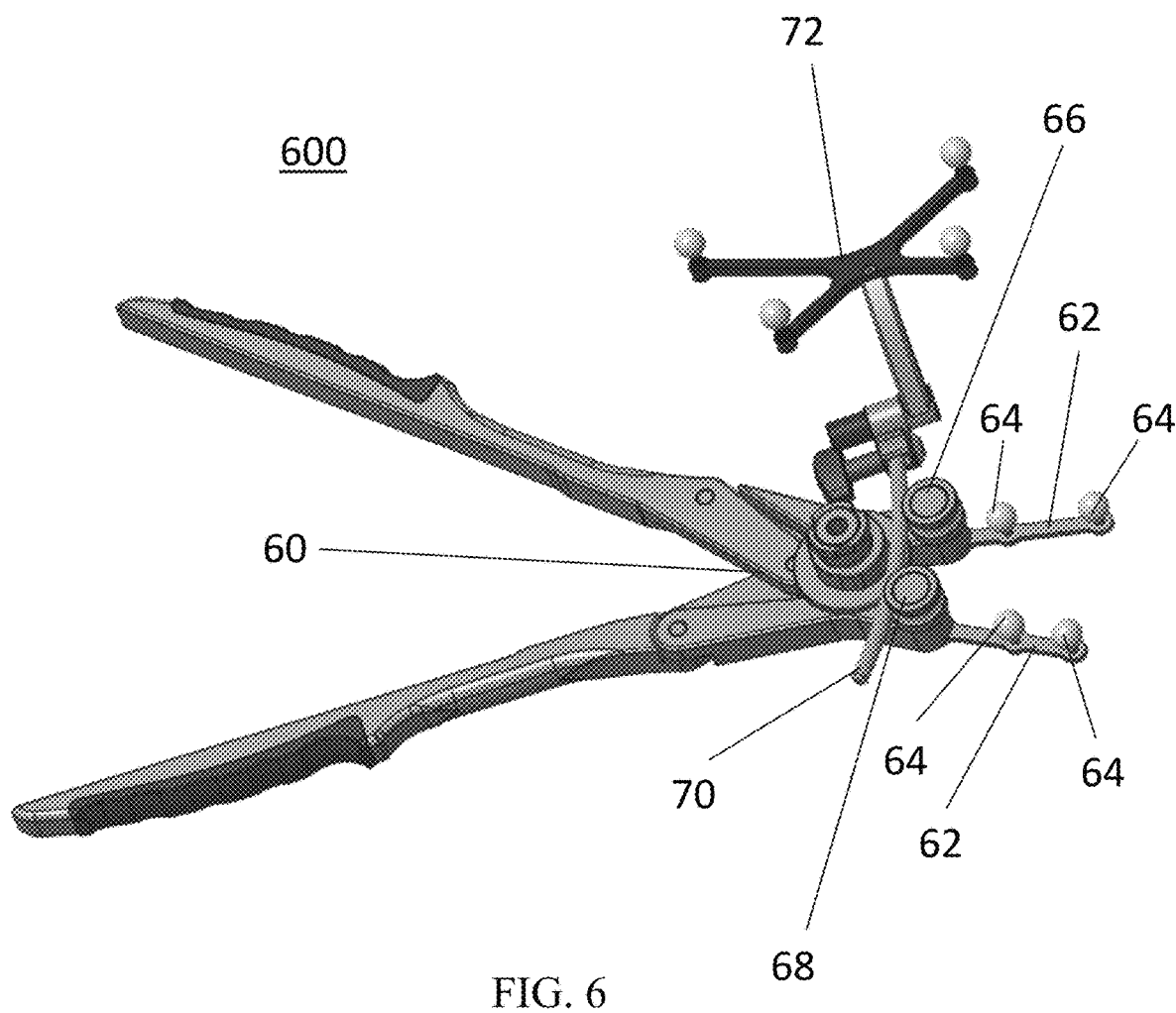
FIG. 6 illustrates a rod bender with a navigation array consistent with the principles of the present disclosure.
Figure 12A:
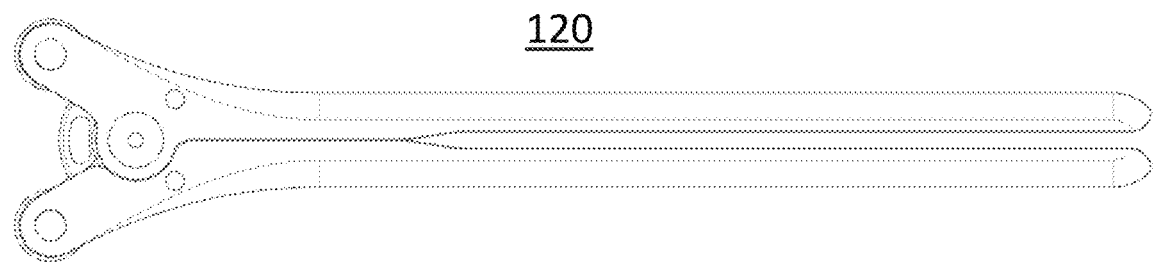
FIGS. 12A, 12B, and 12C illustrate views of a rod bender having a single pivot point consistent with the principles of the present disclosure.
Figure 12B:
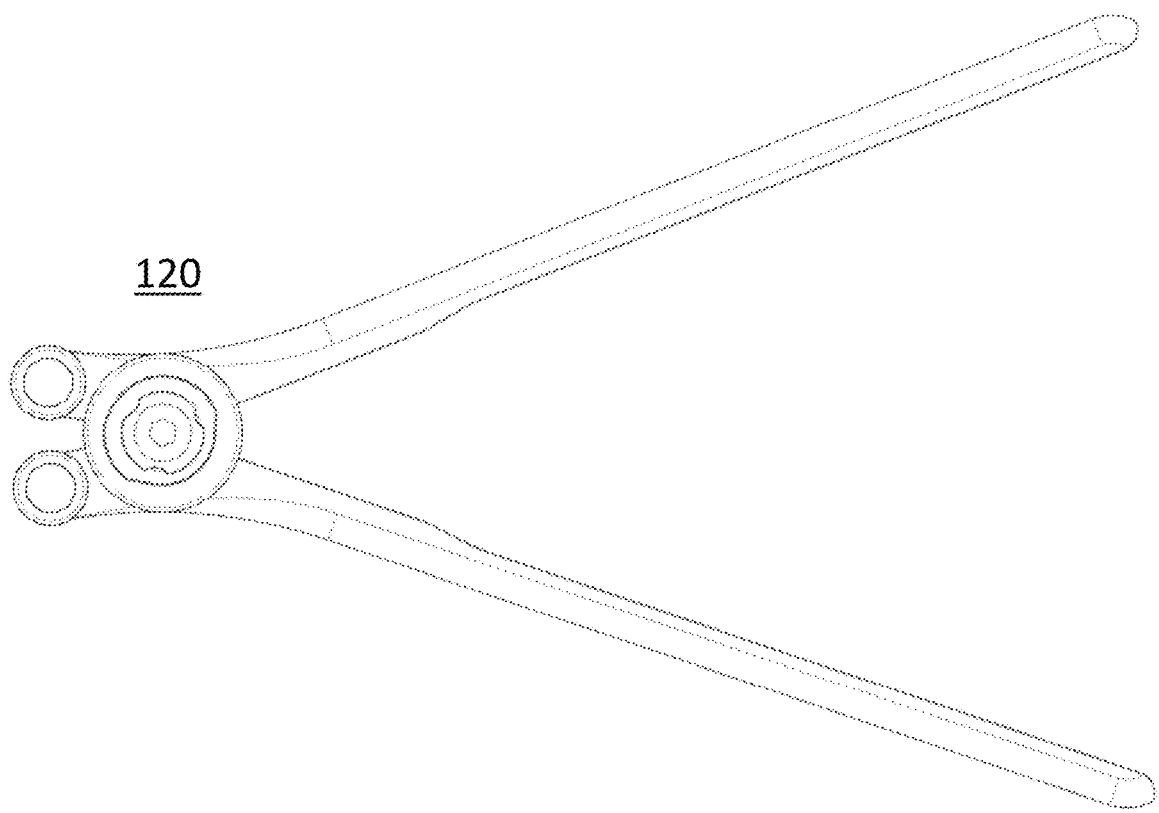
Figure 12C:
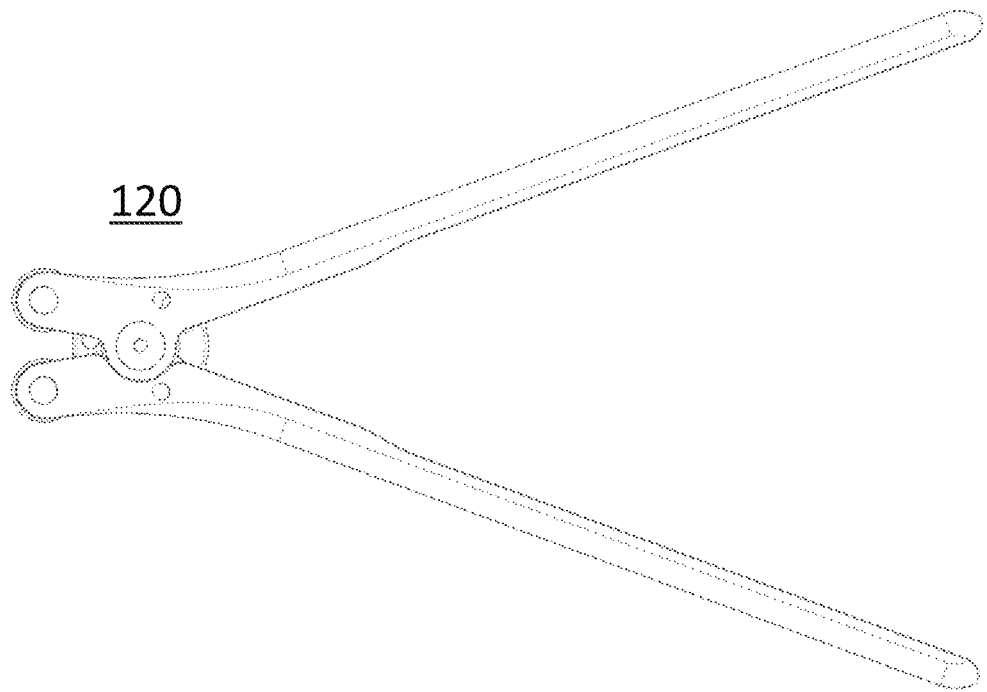

FIG. 6 illustrates an embodiment consistent with the principles of the present disclosure. System 600 may include a rod bender 60 having navigation arrays 62. System 600 may also include rod 70. Navigation arrays 62 may have navigation markers 64 that are arranged in a predetermined manner in order to be recognized and tracked by a navigation system. Rod bender 60 may be similar to rod bender 10 with the addition of navigation markers 64 that may be visible to camera, such as a cameras 92 shown in FIG. 9. In this embodiment navigated markers 64 are attached to bending instruments or rod bender 60 to monitor the displacements of rolling elements 66, and 68 which result in the contour of the rod, for example rod 70. Rod 70 may have a reference array 72 attached that is visible and trackable to the camera and navigation system to determine if rod 70 is being bent according to the planned rod design. In addition, navigation arrays 62 may be attached in a similar manner to a rod bender 120 as shown in FIGS. 12A-12B. Rod bender may differ from rod bender 60 in that rod bender 120 may have a single pivot point as opposed to the multiple pivots of rod bender 60.

Figure 7A:
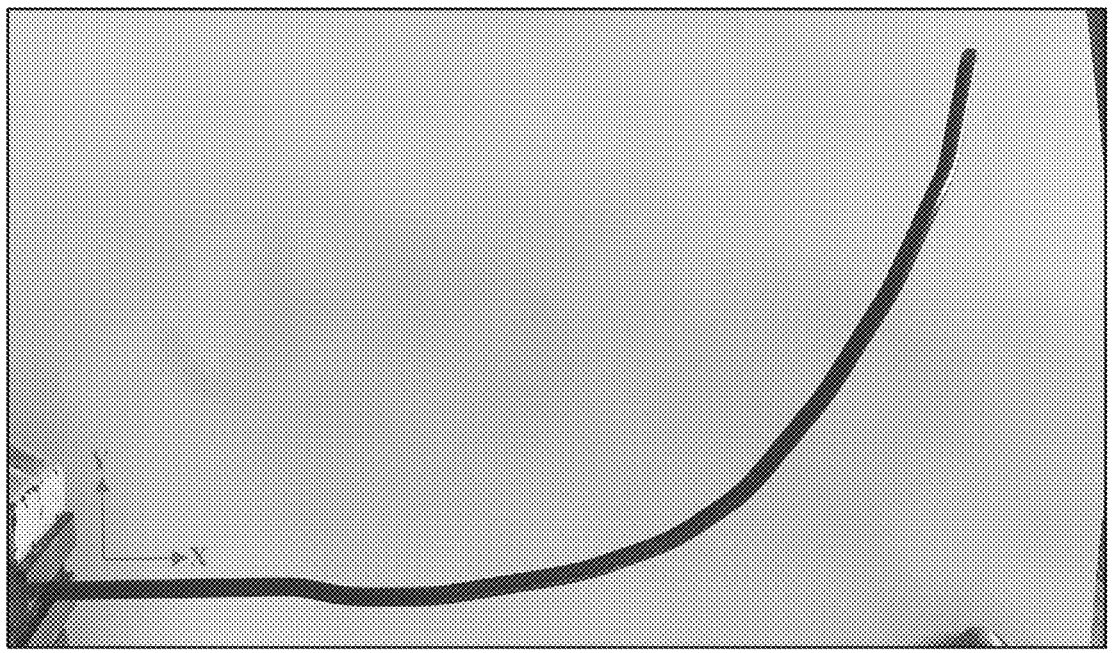
FIGS. 7A and 7B illustrate rod reconstruction through rotated images consistent with the principles of the present disclosure.
Figure 7B:
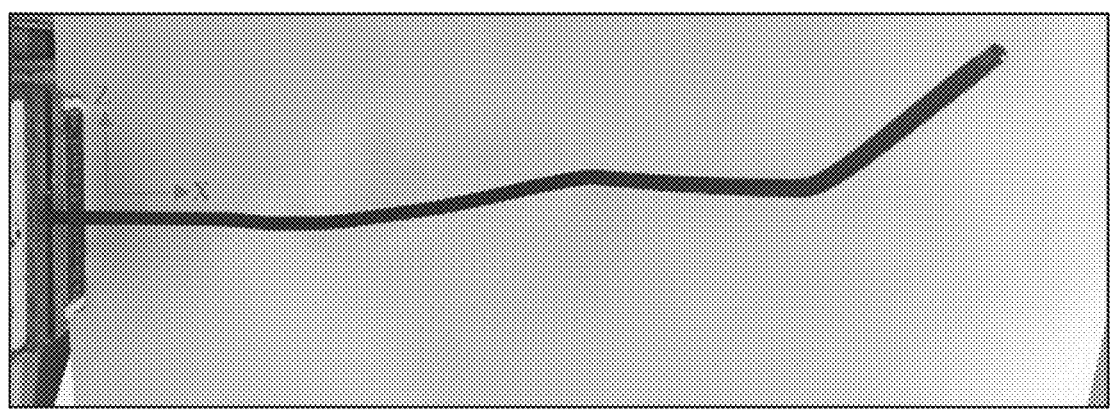
Figure 8:
FIG. 8 illustrates a reconstructed rod using the images of FIGS. 7A and 7B consistent with the principles of the present disclosure.

FIGS. 7A and 7B show a bent rod in different orientations to allow for a rotated image contour reconstruction. In this embodiment, images are taken in two orientations, one in an X-Y plane (FIG. 7A) and one in a X-Z plane (FIG. 7B). The rod is rotated within the field of view of one or more cameras a fixed angle and images are taken before and after rotation. One or multiple sequences of images and rotations can be taken. First, the images are processed to create a 2D planar reconstruction of the central axis of the rod. The boundary edges of the rod are first identified and the central axis of the rod is calculated as the average of the boundaries. As shown in FIG. 8, the 2D planar reconstructions of the rod are then projected against each other to complete the 3D reconstruction. If the images are 90° from each other, coordinates can be directly mapped from one image onto the other as the missing $3^{rd}$ dimension.

Figure 9:
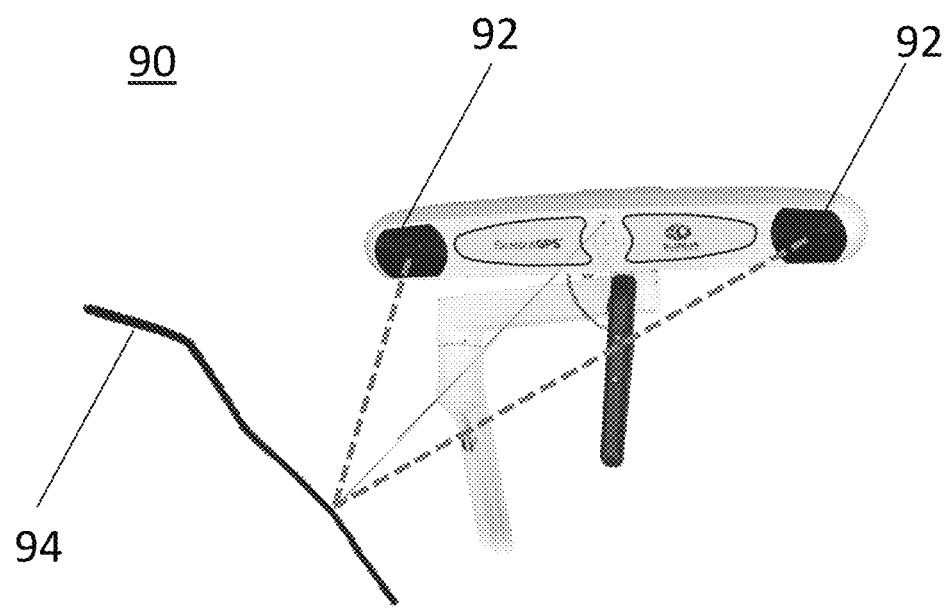
FIG. 9 illustrates stereoscopic image contour reconstruction consistent with the principles of the present disclosure.

FIG. 9 illustrates a stereoscopic image contour reconstruction of a bent rod consistent with the principles of the present disclosure. System 90 includes cameras 92 and rod 94. Rod 94 may be held within the field of view of cameras 94 offset from each other by a fixed distance. One set of images from each camera 92 can be taken of rod 94 at a single position, or multiple images can be taken as rod 94 is moved and rotated within the field of view of cameras 94. The offset between cameras 92 enables triangulation of the surface and centroid of rod 94, enabling 3D reconstruction. Rod 94 may have an infrared-reflective coating to enable tracking with infrared camera systems 92.

Figure 10:
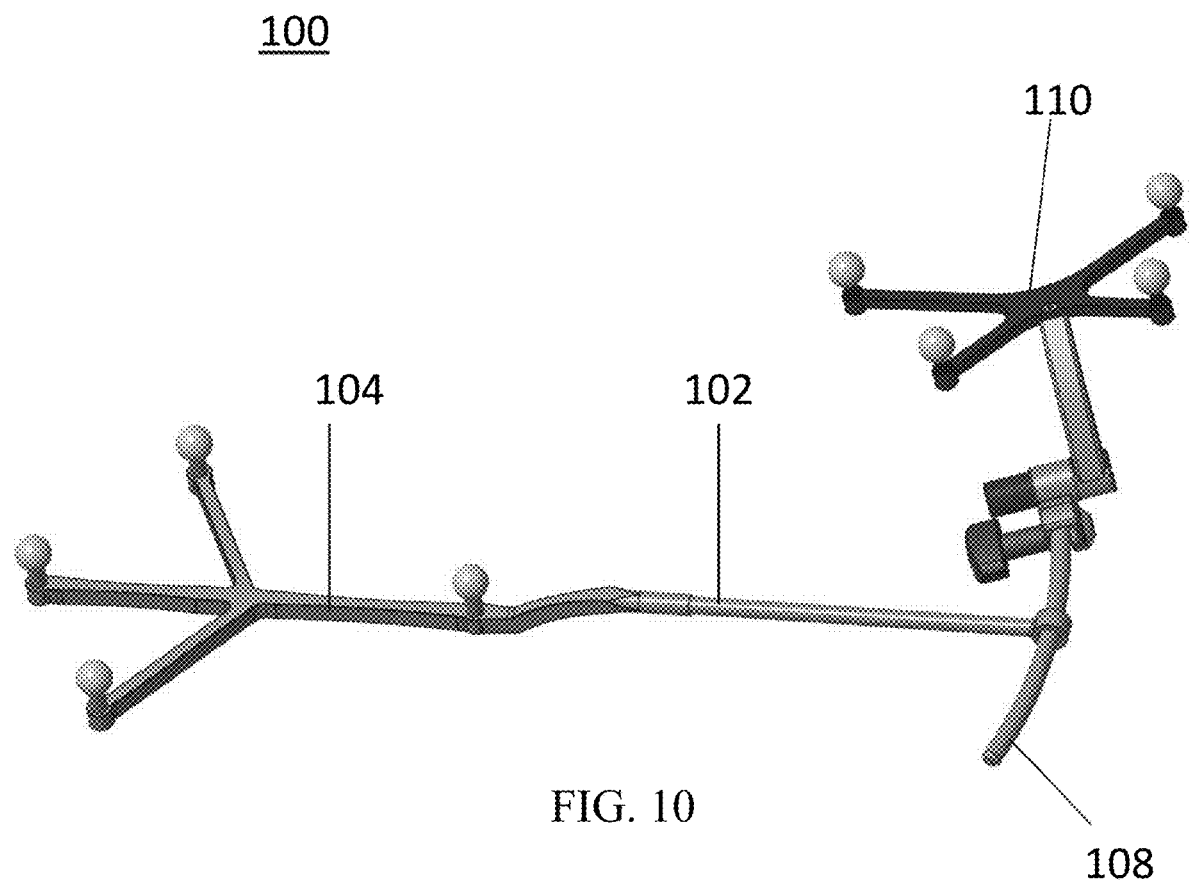
FIG. 10 illustrates a navigated tracing instrument consistent with the principles of the present disclosure.
Figure 11:
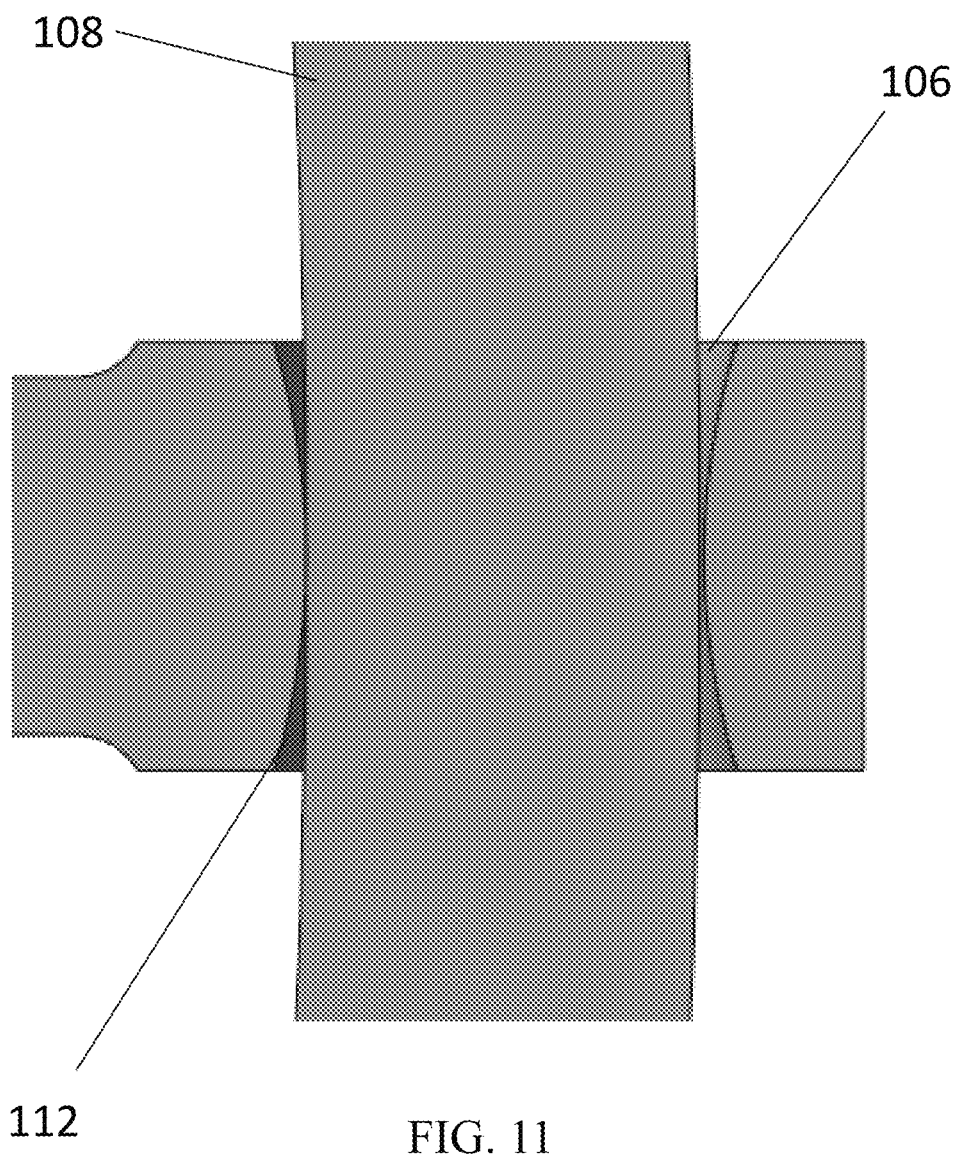
FIG. 11 illustrates a portion of the navigated tracing instrument of FIG. 10 consistent with the principles of the present disclosure.

FIG. 10 illustrates a navigated tracing instrument for use in reconstruction of the bent rod. System 100 may include a navigated instrument 102. Navigated instrument 102 may include an array 104 with a hole 106 sized to closely accept a rod 108 and is moved over rod 108 to establish its center in 3D space. Rod 108 may be fixed in space or have a reference array 110 attached to its base to establish its coordinate system with respect to array 104. As shown in FIG. 11, hole 106 may have a curved or toroidal internal surface 112 to accommodate bends in rod 106.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

What is claimed is:

1. A rod bender system comprising:
    a first handle arm and a second handle arm coupled to a first pivot point; and
    a body portion coupled to the first handle arm at a second pivot point and the second handle arm coupled to the body portion at a third pivot point,
    a navigated tracing instrument having a navigated instrument that includes an array and a through hole;
    wherein the body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion,
    wherein a spinal rod having a third navigation array having one or more optical markers is positioned between the first and second rolling elements and the barrel, and
    wherein a shape of the rod as it is being bent is trackable by a camera system using the optical markers and a three dimensional reconstruction of the rod is created using tracked positions of the optical markers,
    wherein the navigated instrument is configured to receive the spinal rod within the through hole, the through hole being configured to have a curved or toroidal internal surface to accommodate bent spinal rods.

2. The rod bender of claim 1, wherein the first and second rolling elements are rotatable.

3. The rod bender of claim 1, wherein the barrel is rotatable.

4. The rod bender of claim 1, wherein the barrel is configured with a plurality of bending surfaces.

5. The rod bender of claim 1, wherein the barrel may be translated on the body portion into different positions for accommodating varying rod diameters.

6. The rod bender of claim 1, wherein first and second handle arms are configured to pivot with respect to each other.

7. The rod bender of claim 1, wherein the first and second rolling elements are configured for conforming to the radius of the rod.

8. A spinal rod bending system comprising:
    an elongated spinal rod;
    a camera;
    a rod bender for manipulating an elongated spinal rod including:
    a first handle arm and a second handle arm coupled to a first pivot point; and
    a body portion coupled to the first handle arm at a second pivot point and the second handle arm coupled to the body portion at a third pivot point,
    a navigated tracing instrument having a navigated instrument that includes an array and a through hole; and
    wherein the body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion,
    wherein a spinal rod having a third navigation array having one or more optical markers is positioned between the first and second rolling elements and the barrel, and
    wherein a shape of the rod as it is being bent is trackable by the camera using the optical markers and a three dimensional reconstruction of the rod is created using tracked positions of the optical markers,
    wherein the navigated instrument is configured to receive the spinal rod within the through hole, the through hole being configured to have a curved or toroidal internal surface to accommodate bent spinal rods.

9. The system of claim 8, wherein the first and second rolling elements are rotatable.

10. The system of claim 8, wherein the barrel is rotatable.

11. The system of claim 8, wherein the barrel is configured with a plurality of bending surfaces.

12. The system of claim 8, wherein the barrel may be translated on the body portion into different positions for accommodating varying rod diameters.

13. The system of claim 8, wherein first and second handle arms are welded to each other at the first pivot point.

14. The system of claim 8, wherein the first and second rolling elements are configured for conforming to the radius of the rod.

15. A method for manipulating a spinal rod comprising:
    providing a rod bender, the rod bender comprising:
    a first handle arm and a second handle arm coupled to a first pivot point;
    a body portion coupled to the first handle arm at a second pivot point and the second handle arm coupled to the body portion at a third pivot point;

a navigated tracing instrument having a navigated instrument that includes an array and a through hole; and wherein the body portion includes a first distal arm and a second distal arm, the first distal arm having a first rolling element and a first navigation array with one or more optical markers, the second distal arm having a second rolling element and a second navigation array with one or more optical markers, and the body portion configured with a barrel positioned on a center portion of the body portion, positioning the spinal rod, having a third navigation array with one or more optical markers attached to a base of the spinal rod, between the rolling elements and the barrel of the rod bender;

actuating the first and second handle arms thereby bending the spinal rod;

tracking a shape of the spinal rod as it is being bent via a camera using the optical markers; and creating a three dimensional reconstruction of the spinal rod using tracked positions of the optical markers, wherein the navigated instrument is configured to receive the spinal rod within the through hole, the through hole being configured to have a curved or toroidal internal surface to accommodate bent spinal rods.

16. The method of claim 15, wherein the first and second rolling elements are rotatable.

17. The method of claim 15, further comprises the step of rotating the barrel.

18. The method of claim 15, further comprising the step of translating on the body into different positions for accommodating varying rod diameters.

19. The method of claim 15, further comprising the step of pivoting the first and second handle arms with respect to each other at the first pivot point.

20. The system of claim 15, wherein the first and second rolling elements are configured for conforming to the radius of the rod.

* * * * *